United States Patent [19]

Chaudhuri et al.

[11] Patent Number: 5,645,859
[45] Date of Patent: Jul. 8, 1997

[54] PROCESS FOR PRODUCING AN ALPHA OR BETA-HYDROXY ACID-VINYLPYRROLIDONE POLYMER, COPOLYMER OR GRAFT POLYMER COMPLEX IN THE FORM OF FREE-FLOWING POWDERS HAVING A HIGH ACID LOADING

[75] Inventors: Ratan K. Chaudhuri, Lincoln Park; Russell B. Biss, Wayne; John J. Merianos, Middletown, all of N.J.

[73] Assignee: ISP Investments Inc., Wilmington, Del.

[21] Appl. No.: 537,566

[22] Filed: Oct. 2, 1995

[51] Int. Cl.⁶ .................................................. A61K 9/14
[52] U.S. Cl. .................... 424/501; 424/78.24; 514/772.5
[58] Field of Search ........................... 424/78.24, 78.25, 424/497, 78.28; 524/808; 514/772.5

[56] References Cited

U.S. PATENT DOCUMENTS

| | | | |
|---|---|---|---|
| 4,889,844 | 12/1989 | Silvetti, Sr. et al. | 424/78.25 |
| 4,950,653 | 8/1990 | Jauw | 514/53 |
| 5,008,106 | 4/1991 | Merianos et al. | 424/78.24 |

FOREIGN PATENT DOCUMENTS 0311281  4/1989  European Pat. Off. .

*Primary Examiner*—Peter F. Kolkosky
*Attorney, Agent, or Firm*—Walter Katz; Marilyn J. Maue; Joshua J. Ward

[57] ABSTRACT

A process is provided for making a free-flowing powder of a complex of an alpha-hydroxy acid (AHA) and/or a beta-hydroxy acid (BHA) and a vinylpyrrolidone (PVP) polymer, copolymer or graft polymers, as the complexing agent, at high acid loadings, preferably 20–60% by weight. The presence of VP polymers, copolymers or graft polymers in the complex reduces the skin irritation effect of the acid when applied to the skin of the user. The process involves applying an aqueous solution or slurry of the acid to PVP, and, substantially immediately thereafter, evaporating the water to form a free-flowing powder of the complex of the acid and VP polymers, copolymers or graft polymers.

17 Claims, No Drawings

PROCESS FOR PRODUCING AN ALPHA OR BETA-HYDROXY ACID-VINYLPYRROLIDONE POLYMER, COPOLYMER OR GRAFT POLYMER COMPLEX IN THE FORM OF FREE-FLOWING POWDERS HAVING A HIGH ACID LOADING

BACKGROUND OF THE INVENTION

1. Field of the Invention

This invention relates to a process for making an alpha or beta-hydroxy acid-polyvinylpyrrolidone complex, and more particularly, to production of such complex in the form of free-flowing powders at high acid loadings.

2. Description of the Prior Art

Cosmetic compositions having an alpha- or beta-hydroxy acid as the active ingredient are well-known in the art. These compositions are useful for treatment of the skin, particularly for anti-aging, improvement in skin tone, reduction of fine line, enhancement of moisture, and development of a smooth skin. Application of such compositions generally results in a younger-looking skin as new cells replace the old. However, to achieve this improvement in skin condition, it is necessary for the user to tolerate the skin irritation caused by the acid present in the product. Accordingly, skin irritation is a major concern to formulators of compositions of alpha and beta-hydroxy acids, particularly at high acid loading levels which can deliver faster and more effective skin peeling. More irritation, furthermore, is perceived by the user as being a more effective treatment.

Accordingly, it is an object of this invention to provide a cosmetic composition of an alpha or beta-hydroxy acid which includes an effective anti-irritant agent therein.

SUMMARY OF THE INVENTION

In accordance with this invention, a process is provided for making a free-flowing powder of a complex of an alpha-hydroxy acid (AHA) and/or a beta-hydroxy acid (BHA) and a vinylpyrrolidone (PVP) polymer, copolymer or graft polymer, as the complexing agent, at high acid loadings, preferably 20–60% by weight. The presence of PVP in the complex reduces the skin irritation effect of the acid when applied to the skin of the user.

The process of the invention involves applying an aqueous solution or slurry of the acid to PVP, and, substantially immediately thereafter, evaporating the water to form a free-flowing powder of the complex of the acid and PVP.

DETAILED DESCRIPTION OF THE INVENTION

A suitable alpha-hydroxy acid is lactic acid, glycolic acid, citric acid, tartaric acid, malic acid, pyruvic acid, azelaic acid and the like. Suitable beta-hydroxy acids include salicylic acid and the like.

Suitable vinylpyrrolidone-complexing agents include PVP itself, either in water-soluble form or in water-insoluble form (crosslinked); or copolymers thereof, e.g. with vinyl acetate or acrylic acid, or graft copolymers thereof, e.g. with $C_1$–$C_4$ alkyl groups, e.g. butene, dodecene, hexadecene, etc.

The process of the invention may be carried out in a fluid bed, by spray drying a solution or slurry, or by tray drying a slurry.

In accordance with one embodiment of the present invention, a fluidized bed containing a charge of PVP powders is reacted with an aqueous solution of concentrated AHA or BHA. The PVP polymer can be obtained from International Specialty Products in the form of a water-soluble or water-insoluble polymer, which has a molecular weight ranging from the K-15 to K-90 designations. These PVP polymers, which generally have a water content of about 5% by weight, or less, and a particle size of about 10 to 100 microns, may be used directly in the process of the invention, or pre-dried, if desired, to reduce its moisture content.

The AHA used herein usually contains about 20–88% by weight acid.

The fluidized bed of PVP powders can be maintained in the fluidized condition by directing a current of dry air through the powders, by mechanical agitation of the powders, or by a combination of both techniques.

The fluidized bed is maintained at a suitable bed (reaction) temperature at which formation of the desired AHA-PVP complex product can occur readily without affecting the powdery state of the PVP polymer, and at which excess water from the acid solution can be quickly removed both from the product and the PVP bed itself. The selected bed temperature also will enhance the formation of a free-flowing powder rather than a gum. Such suitable reaction temperatures range from about ambient temperature to 90° C., preferably about 80° C.

The aqueous concentrated acid solution preferably is contacted with the PVP powders as finely divided droplets of liquid. Such desired droplets may be formed by pumping the aqueous solution through a spray nozzle and onto the PVP bed at a selected rate and for a predetermined period of time. Any spray nozzle capable of producing a fine dispersion of droplets may be used for this purpose. If necessary, however, a stream of air may be introduced into such nozzle with the solution to assist in atomizing the solution into finely divided droplets.

The spray solution of aqueous acid thus formed preferably is introduced into the fluidized bed of PVP powders at a selected rate such that excess water can be removed therein during formation of the complex without retaining free acid therein. A suitable feed rate for introduction of the acid solution is about 5–50 g/minute/kg PVP, preferably about 5–25 g/minute/kg PVP. Under these flow rate conditions, a free-flowing powder of the desired AHA-PVP complex is obtained containing about 20–60% by weight, preferably 25–50%, and about 2% or less water therein. The powder also may contain about 0.1–2% by weight of a flow enhancer, such as fumed silica, if desired.

In the preferred form of the process of the invention, the spray solution of acid is directed onto the PVP bed for a period sufficient to form a free-flowing powder having an acid content of about 25–50% by weight, which is indicative of a complex having a 1:1 molar ratio of PVP to acid. At this point in the process, the feed is discontinued to preclude excess water and/or free acid from forming on the free-flowing powder which can cause it to become gummy. The appearance of a gummy product is indicative of the presence of excess water and/or free acid in the product.

The spray solution of acid may be directed onto the fluidized bed as a vertical, horizontal or by downward flow of droplets.

If a fluidizing air stream is used to create the fluid bed, it is usually directed upwardly against the PVP powders. Such air currents also can assist in carrying water away from the bed. The fluidized state of the bed also may be maintained using mechanical agitation, or a combination of both air and mechanical means.

The process of the invention can be carried out in one or two steps, i.e. removal of water from the product and bed can take place either (a) simultaneous with or after mixing of the reaction components in the same apparatus, or (b) in a downstream drying step, or (c) by a combination of both steps. The particular method of drying will depend upon the type of equipment used. For example, if a fluidized bed mixer is used, such as a plowshare, belt screw or paddle mixer, then the moist acid-PVP product can be dried further in a separate dryer. This sequence is characterized as a two-step process. Any suitable dryer can be used for this purpose, such as a vacuum, radiant heat or contact dryer.

Furthermore, if desired, application of the spray acid solution onto the PVP bed, followed by downstream drying, may be carried out in several stages in order to increase the acid content of the product towards the desired 3:1 to 1:1 molar ratio, and to reduce its water content.

Moreover, a fluid bed dryer may be used in the process which has the dual capabilities of providing both the fluidized bed and drying functions. Accordingly, drying of the product will begin and be completed during reaction between the PVP charge and the aqueous acid solution. Such a process may be considered as taking place in a one-step.

Preferably, reaction and dehydration are continued until the product reaches a desired acid content, suitably about 20–60% acid, and usually about 25–50%, with less than about 2.5% water, generally about 1%. However, it is essential that the product remain in the free-flowing state after completion of addition of the acid solution.

The size of the fluidized bed reactor, the rate of addition of the AHA or BHA solution, and the reaction times will vary with the particular equipment used, as well as the concentration of the acid solution and the reaction temperature, keeping in mind the purposes intended to be achieved with respect to each of these process parameters.

Alternatively, the process of the invention may be practiced by spray drying or tray drying, in the conventional manner known in the art.

However, it is believed that the following examples will illustrate the employment of these parameters to provide a process which can be used for the commercial production of the desired acid-PVP products. These examples, of course, are given by way of illustration only, and are not to be construed as limiting the invention.

EXAMPLE 1

An 88% aqueous solution of L-lactic acid was spray fed onto a UniGlatt fluid bed unit containing 300 g of PVP-CI (K-30 grade) supported on a 100-mesh dutch weave screen. A feed rate of about 1.1 cc/hr/g lactic acid was used at an inlet air temperature of 80° C. The product temperature was about 45° C. A 22% lactic acid loading was achieved in the complex, which was a free-flowing powder. The moisture level of the product was 1.85%.

EXAMPLE 2

A crosslinked PVP (Polyplasdone XL) charge of 250 g and the concentrated (88%) lactic acid solution was used. A 28.8% loading at 1.2% moisture was achieved within 40 minutes of operation.

EXAMPLE 3

The procedure of Example 1 was repeated, however, after about 20 minutes, a fumed silica flow enhancer (Cabo-Sil) was added at about a 1% concentration. A 5 minutes dryout period achieved a 1.3% moisture with a final loading of 28.5% lactic acid.

EXAMPLE 4

The run was conducted with Ganex® P-904, a copolymer of 90 wt. % polyvinylpyrrolidone with 10% grafted butene. 150 g. of the graft polymer was charged to the unit. During the 50 minute run, the volume was reduced by about one-half of lactic acid feed. The copolymer loading of 32.5 wt. % was achieved.

EXAMPLE 5

A 50/50 blend of polyvinylpyrrolidone K-30 (PVP-CI) and crosslinked PVP (Polyplasdone® XL) was charged to the unit. A loading of 29.6% lactic acid was achieved. Then ½ of the product was withdrawn from the bowl and approximately ½% silica flow enhancer was added and the unit restarted. A final loading of 32.5% lactic acid was achieved after 55 minutes.

EXAMPLE 6

Crosslinked PVP (Polyclar®) 50 g was added to a well-stirred solution of lactic acid (88%, 57 g) and water (135 ml). After thorough mixing, the slurry was poured onto a tray and the slurry was dried under low vacuum at 50° C. The product was a free-flowing powder having a loading of 49.6% lactic acid.

EXAMPLE 7

Crosslinked PVP 20 g was added to a well-stirred solution of glycolic acid (70%, 29 g) and water (60 ml) After thorough mixing, the slurry was poured onto a tray and dried under low vacuum at 50° C. The product was a free-flowing powder with 48.6% glycolic acid.

EXAMPLE 8

Example 5 was repeated except the drying process was spray drying. Similar results were obtained.

EXAMPLE 9

Example 6 was repeated except the drying process was spray drying. Similar results were obtained.

EXAMPLE 10

Example 6 was repeated except that glycolic acid (70% aqueous solution, 29 g) was used. The product was a free-flowing powder having a loading of 48.6% glycolic acid.

What is claimed is:

1. A process for the production of alpha or beta-hydroxy acid-vinylpyrrolidone (PVP) polymer, copolymer or graft polymer complexes in the form of free-flowing powders containing about 20–60% by weight of said acid and less than 2.5% by weight of water which comprises applying an aqueous solution or slurry of said acid to said PVP polymer, copolymer or graft polymer, substantially immediately thereafter, evaporating the water to form a free-flowing powder of the complex of the acid and said PVP polymer, copolymer or graft polymer having said composition.

2. A process according to claim 1 which comprises reacting a fluidized bed of PVP maintained at a reaction temperature of about ambient temperature to about 95° C. with finely divided droplets of a 20% to 88% by weight aqueous solution of said acid, and drying the product.

3. A process according to claim 2 wherein the acid feed rate is about 5–50 g/min/kg PVP.

4. A process according to claim 2 wherein the PVP is selected from water soluble and water-insoluble PVP powders in a range of molecular weights corresponding to the designation K-15 to K-120.

5. A process according to claim 1 wherein said PVP polymer is a water soluble PVP polymer.

6. A process according to claim 1 wherein said PVP polymer is a crosslinked PVP polymer.

7. A process according to claim 1 wherein said PVP is a copolymer of VP and vinyl acetate.

8. A process according to claim 1 wherein said PVP is a graft polymer of VP a $C_1$–$C_4$ alkyl monomer.

9. A process according to claim 8 wherein said PVP is a graft polymer of VP and butene.

10. A process according to claim 1 wherein the product contains about 20–40% by weight acid.

11. A process according to claim 1 wherein the alpha-hydroxy acid is selected from lactic acid, glycolic acid, citric acid, tartaric or malic acid, and the beta-hydroxy acid is salicylic acid.

12. A process according to claim 1 wherein said process is carried out by spray or tray drying or in a fluidized bed.

13. A free-flowing powder of a complex of an alpha-hydroxy acid or a beta-hydroxy acid and a polyvinylpyrrolidone (PVP) polymer, copolymer or graft polymer complexing agent which contains about 20–60% by weight of said acid and less than 2.5% by weight of water.

14. A powder according to claim 13 wherein said alpha-hydroxy acid is lactic acid, glycolic acid, citric acid, tartaric acid or malic acid, and said beta-hydroxy acid is salicylic acid.

15. A powder according to claim 13 wherein said PVP is a water-soluble or water-insoluble PVP.

16. A powder according to claim 13 which contains about 0.1–2% by weight of a flow enhancer.

17. A powder according to claim 16 wherein said flow enhancer is fumed silica.

* * * * *